United States Patent [19]

Hammann et al.

[11] Patent Number: 4,914,216

[45] Date of Patent: Apr. 3, 1990

[54] AMYCIN AND ITS DERIVATIVES, A PROCESS FOR THEIR PREPARATION, AND THEIR USE

[75] Inventors: Peter Hammann, Kelkheim; Susanne Grabley, Königstein/Taunus; Hartmut Voelskow, Hattersheim am Main; Burkhard Sachse, Kelkheim; Wolfgang Raether, Dreieich; Carlo Giani, Frankfurt am Main; Gerhard Seibert, Darmstadt, all of Fed. Rep. of Germany

[73] Assignee: Hoechst Aktiengesellschaft, Frankfurt am Main, Fed. Rep. of Germany

[21] Appl. No.: 136,393

[22] Filed: Dec. 22, 1987

[30] Foreign Application Priority Data

Dec. 24, 1986 [DE] Fed. Rep. of Germany ....... 3644374
Jan. 8, 1987 [DE] Fed. Rep. of Germany ....... 3700325

[51] Int. Cl.$^4$ .................. C07D 321/00; C07D 323/00
[52] U.S. Cl. .................................. 549/267; 549/269; 549/270
[58] Field of Search .................. 549/270, 269, 267

[56] References Cited

U.S. PATENT DOCUMENTS 4,703,128 10/1987 Beppu et al. .................. 549/270

OTHER PUBLICATIONS

Chemical Abstract 105:168550q (Nov. 10, 1986).

Primary Examiner—Asok Pal
Attorney, Agent, or Firm—Finnegan, Henderson, Farabow, Garrett and Dunner

[57] ABSTRACT

*Streptomyces parvullus*, DSM 3816, produces on aerobic fermentation new antibiotics which are distinguished by antimicrobial activity even after derivatization.

3 Claims, No Drawings

AMYCIN AND ITS DERIVATIVES, A PROCESS FOR THEIR PREPARATION, AND THEIR USE

Amycin and its derivatives, a process for their preparation, and their use

British Patent 1,254,721 describes the preparation of the macrolide antibiotic niphimycin by fermentation of *Streptomyces hygroscopicus*. Niphimycin can be used, in particular, as an antifungal agent.

It has now been found that the strain *Streptomyces parvullus*, which has been deposited at the German collection of microorganisms under the number of DSM 3816, synthesizes a new antibiotic, amycin. Amycin may have wide uses as a pharmaceutically active substance. Although the structural formula of amycin is similar to that of niphimycin, it has been found, surprisingly, that it has, in particular, a significantly more potent antifungal action. Derivatives of amycin can also be used as pharmaceutically active substances.

Hence the invention relates to:
1. Compounds of the general formula Ia

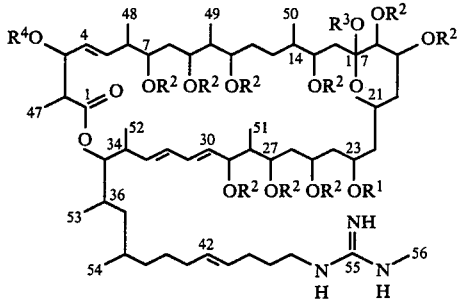

in which, in each case independently of one another,
$R^1$ and $R^2$ are hydrogen or a malonyl group, not more than one $R^2$ substituent representing a malonyl group, $R^3$ and $R^4$ denote hydrogen or $C_1$–$C_6$ alkyl or allyl, and the compounds of the formula IIa which are unsaturated in the 22/23 position,

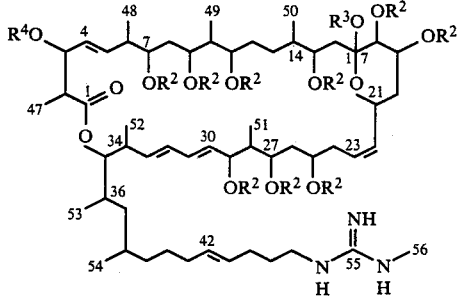

excepting the combinations in compounds of the formula Ia in which
(a) $R^1$ is malonyl and all $R^2$, $R^3$ and $R^4$ are hydrogen,
(b) $R^1$ is malonyl, all $R^2$ and $R^4$ are hydrogen, and $R^3$ is methyl, or
(c) $R^1$, all $R^2$ and $R^4$ are hydrogen, and $R^3$ is methyl, including, furthermore, compounds of the formula Ib,

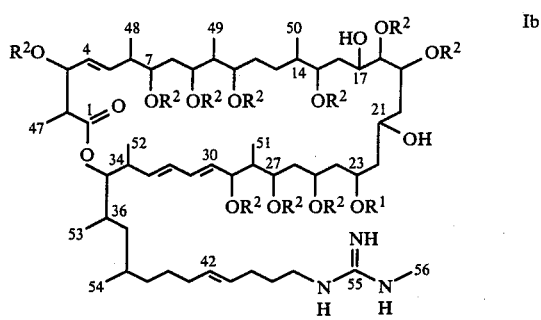

in which $R^1$ and $R^2$ have the abovementioned meaning, as well as the compounds of the formula IIb which are unsaturated in the 22/23 position.

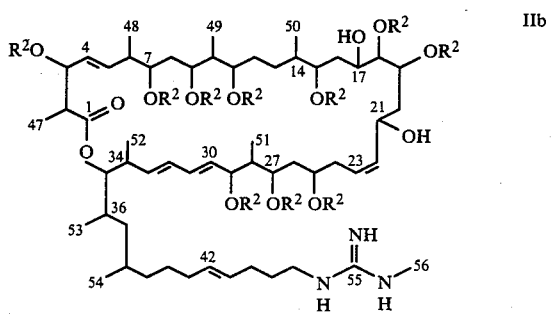

2. A process for the preparation of the compounds of the general formulae Ia, IIa and Ib and IIb, which comprises
(a) cultivation of *Streptomyces parvullus*, DSM 3816, and of its variants and mutants, in a nutrient medium until the compound of the formula Ia in which $R^1$ and one $R^2$ radical denote malonyl, and $R^3$ and $R^4$ denote hydrogen, and the compound in which $R^1$, all $R^2$, $R^3$ and $R^4$ denote hydrogen, accumulate in the culture, and where appropriate
(b) isolation and derivatization of the latter.

3. The use of the compounds of the general formulae Ia, IIa and Ib and IIb as antimicrobial agent.

The invention, especially its preferred embodiments, is described in detail hereinafter. The invention is also defined in the patent claims.

On aerobic fermentation in a nutrient medium which contains a source of carbon, a source of nitrogen and the customary inorganic salts, *Streptomyces parvullus* DSM 3816 produces amycin, which has antimicrobial activity and in which $R^1$ and one $R^2$ radical denote malonyl, and $R^3$ and $R^4$ denote hydrogen, as well as the demalonyl compound in which $R^1$, all $R^2$, $R^3$ and $R^4$ are hydrogen. The $R^2$ malonyl group in amycin may be bonded to one of the possible free hydroxyl groups in the molecule. Of course, it is also possible, in place of the strain DMS 3816 to use its mutants and variants as long as they synthesize at least one of these compounds. Mutants of this type can be generated in a manner known per se, by physical means, for example irradiation such as with ultraviolet or X-rays, or chemical mutagens such as, for example, ethyl methanesulfonate (EMS) or 2-hydroxy-4-methoxybenzophenone (MOB). fermentation are assimilable carbohydrates and sugar alcohols such as glucose, lactose or D-mannitol, as well as carbohydrate-containing natural products, such as malt extract. Suitable nitrogen-containing nutrients are: amino acids, peptides and proteins, as well as their degradation products, such as peptones or tryptones, also meat extracts, milled seeds, for example of corn, wheat, beans, soybean or the cotton plant, distillation residues from the production of alcohol, meat meals or yeast extracts, as well as ammonium salts and nitrates. Examples of other inorganic salts which the nutrient solution may contain are chlorides, carbonates, sulfates or phosphates of the alkali metals or alkaline earth metals, iron, zinc and manganese.

The formation of amycin takes place particularly well in a nutrient solution which contains soybean meal and mannitol, in particular 2% of each, based on the total weight of the nutrient solution. The fermentation is carried out aerbically, that is to say, for example, submerged with shaking or stirring in shaken flasks or fermenters, where appropriate with the introduction of air or oxygen. The fermentation can be carried out in a temperature range from about 18° to 35° C., preferably at about 25° to 30° C., in particular at 28° to 30° C. The pH range should be between 6 and 8, advantageously between 6.5 and 7.5. Under these conditions, in general the culture broth shows a detectable antimicrobial action after 1 to 5 days.

The cultivation is advantageously carried out in several stages, i.e. one or more precultures are initially prepared in a liquid nutrient medium and are then transferred into the actual production medium, the main culture, for example in the ratio by volume 1:10. The preculture is obtained, for example, by transferring a sporulated mycelium into a nutrient solution and allowing it to grow for about 48 to 72 hours. The sporulated mycelium can be obtained by allowing the strain to grow for about 7 days on a solid or liquid nutrient medium, for example, yeast-malt agar.

The course of the fermentation can be monitored by means of the pH of the culture, or the mycelium volume, by thin-layer chromatography or checking the biological activity. Amycin and the corresponding demalonyl compound are present both in the mycelium and in the culture filtrate.

The said compounds are isolated from the culture medium by known methods which take account of the chemical, physical and biological properties of the products. It is possible to use, for testing the antibiotic concentration in the culture medium or in the individual isolation stages, thin-layer chromatography, for example on silica gel with n-butanol/acetic acid/water as mobile phase, the amount of antimicrobial substance which is formed expediently being compared with a calibration solution.

To isolate the compounds, first the culture broth and mycelium are extracted with organic solvents such as, for example, chloroform, ethyl acetate etc. in order to remove the non-polar impurities. Subsequently, extraction is carried out with a more polar solvent, for example lower alkanols or mixtures of chloroform and ethyl acetate with a lower alkanol.

Isolation of the pure product is preferably carried out on suitable media such as, for example, silica gel, alumina or ion exchangers, with subsequent elution using organic polar solvents or solvent mixtures such as, for example, ethyl acetate, mixtures of ethyl acetate and a lower alkanol, where appropriate with water, or with salt gradients which are suitable for ion exchangers, such as, for example, sodium chloride or tris-HCl, and collection of the fractions with antibiotic activity.

Pure amycin is amorphous. The compound is soluble in polar solvents such as, for example, water, methanol and DMF, moderately soluble in, for example, higher alcohols, and insoluble in non-polar solvents such as, for example, chloroform, ethyl acetate or ether.

Conversion into amycin derivatives is carried out in a manner known per se. Thus, it is possible to prepare the $R^3$ alkyl/allyl compounds by treatment of amycin with the appropriate alcohols under acidic conditions in organic solvents. Examples of suitable alcohols are $C_1$-$C_6$ alkanols or allyl alcohol. It is also possible to use long-chain alkanols but the yield of the desired compound decreases with increasing chain length. It is preferable to use the alcohol itself as solvent. The reaction can take place at $-20°$ to $40°$ C., but preferably at room temperature. The reaction time depends on the alcohol and lasts approximately 10 minutes to 4 hours.

Elimination of the malonic hemiester in amycin under basic, acidic or neutral conditions in water or lower alcohols, such as, for example, methanol, ethanol, isopropanol etc., yields the demalonyl compound. The compound dehydrated in the 22/23 position (formula IIa) is obtained as an additional compound. The temperature for this reaction can be $-30°$ to $40°$ C. However, room temperature is once again preferred.

Derivatization of the demalonyl compound with the appropriate alcohols under acidic conditions results in the $R^3$ alkyl/allyl acetals. The statement already made above in connection with the preparation of the $R^3$ alkyl compounds applies equally to the suitability of the alcohols. The $R^3/R^4$ dialkyl derivative is also produced in this reaction.

The hemiacetal can be opened by reduction, for example using borohydrides and aluminum hydrides, such as $NaBH_4$ or lithium aluminum hydride, in polar solvents such as water or lower alcohols etc.

The derivatives of amycin also show an antimicrobial action, in particular against bacterial organisms and fungi which are pathogenic for humans, phytopathogenic or spoil foodstuffs. The action of amycin and its derivatives is better than that of niphimycin, and the former are distinguished by reduced toxicity and greater solubility in water. The compounds are stable in the solid state and in solution in the pH range 3 to 9, in particular 5 to 8, and can thus be incorporated into customary pharmaceutical formulations.

The invention is further illustrated in the examples which follow. Unless stated otherwise, percentage data relate to weight, and mixing ratios of liquids relate to volume.

EXAMPLES

1

(a) Preparation of a suspension of *Streptomyces parvullus* DSM 3816 spores

Composition of the nutrient medium:
12.5 g glycerol
1.0 g arginine
1.0 g NaCl
1.0 g $K_2HPO_4$
0.5 g $MgSO_4.7H_2O$
15.0 g agar
2.5 ml trace element solution
1 liter $H_2O$ dist.
Composition of the trace element solution
30 g $CaCl_2.2H_2O$
1.0 g iron(III) citrate 0.2 g MnSO$_4$
0.1 g ZnCl$_2$
0.025 g CuSO$_4$.5H$_2$O
0.02 g Na$_2$B$_4$O$_7$.10H$_2$O
0.004 g CaCl$_2$
0.01 g Na$_2$MoO$_4$.2H$_2$O
1 liter H$_2$O dist.

Slant tubes containing the abovementioned nutrient medium are inoculated with DSM 3816 and incubated at 30° C. for 8 days. The spores are rinsed out of the tubes using 3 ml of a solution of 0.9% NaCl and 0.1% Tween 80, and are stored at 4° C. until inoculated.

(b) Preparation of a preculture of DSM 3816 in Erlenmeyer flasks

5 Erlenmeyer flasks of 300 ml capacity are each charged with 100 ml of nutrient solution (40 g of glucose, 30 g of soybean meal, 2.5 g of NaCl, 2.5 g of CaCO$_3$, in 1 liter of dist. water, pH 7.5 before sterilization), and each is inoculated with 1.5 ml of the suspension of spores which has been prepared, as freshly as possible, as in 1(a). Incubation is carried out on a shaker (180 rpm) at 30° C. for 72 h.

(c) Preparation of a main culture of DSM 3816

A 300 ml Erlenmeyer flask containing 100 ml of nutrient solution (20 g of soybean meal, 20 g of mannitol, in 1 liter of dist., water, pH 7.5 before sterilization) is inoculated with 3 ml of the preculture from 1b, and incubation is carried out at 30° C. on a shakr (180 rpm). Maximum production is reached after about 48 h to 72 h. The yields are 200 to 300 mg/l.

(d) Cultivation of DSM 3816 in a fermenter

A fermenter of 13 liter capacity is operated under the following conditions:

7 liters of air per minute are introduced into the culture liquid (medium as in Example 1c) at an incubation temperature of 30° C. and with the stirrer at 300 rpm. The fermenter is inoculated with 500 ml of the preculture (see 1b). The optimum production is reached after about 48 to 76 h. The yields are about 300 to 400 mg of amycin/l.

2. Working up to 20 liters of culture broth

The culture broth is filtered. The mycelium is washed with ethyl acetate (3×500 ml) and then extracted with methanol (3×500 ml). The alcohol is removed by distillation in vacuo, and the resulting residue (27 g) is chromatographed on two silica gel columns (500 g) using ethyl acetate/methanol/water (6:1:1; v:v:v) (medium pressure chromatography). 8.4 g of amycin are obtained.

The culture filtrate is washed with 2×20 liters of ethyl acetate and then extracted with 3×20 liters of chloroform/methanol (1:1, v:v). The combined organic phases are concentrated in vacuo to a syrup (78 g). The residue is chromatographed on silica gel using ethyl acetate/methanol/water 6:1:1 as above. 5.3 g of amycin and 450 mg of the corresponding demalonyl compound in which $R^1$, all $R^2$, $R^3$ and $R^4$ denote hydrogen are obtained.

Amycin: MS (FAB)/MH$^+$ = 1229.

$^{13}$C NMR(75 MHz) in CD$_3$OD: δ=176.9, 174.2, 174.1, 171.7, 171.3, 156.6, 99.1 ppm.

IR(KBr)(cm$^{-1}$)=3400, 2860, 1720, 1640, 1600, 1460, 1385.

Demalonyl compound: MS (FAB): MH$^+$ = 1057.

$^{13}$C NMR(75 MHz) in CD$_3$OD: δ=177.1, 156.6, 99.1 ppm.

3. Preparation of the demalonyl compound ($R^1$, all $R^2$, $R^3$ and $R^4$=H) and the derivative dehydrated in the 22/23 position 1 g of amycin (0.81 mmol) is stirred with 100 mg of sodium hydride in 75 ml of methanol at room temperature for 24 hours. After neutralization with 5N hydrochloric acid, the alcohol is removed by distillation in vacuo. The resulting syrup is chromatographed on 100 g of silica gel using ethyl acetate/methanol/water (15:2:1, 800 ml and 8:2:1; v:v:v). Crystallization from methanol/ethyl acetate yields 720 mg (72%) of the demalonyl compound. In addition, 80 mg (8%) of the 22/23-dehydrated compound (formula IIa) are obtained.

22/23-dehydrated compound: MS (FAB): MH$^+$ = 1039

4. Preparation of $R^3$ alkylamycin 1 g of amycin (0.81 mmol) is stirred with a mixture of 1.5 ml of acetyl chloride and 75 ml of methanol at room temperature for 15 min. After neutralization with 5N NaOH, the mixture is concentrated in vacuo to a syrup. Chromatography by HPLC on RP C-18 [30 min, methanol/H$_2$O (6:4; v:v) and a methanol/water gradient from 6:4 to 99:1 in 10 min, and 30 min with methanol/water 99:1] yields 760 mg (70%) of methylamycin.

MS (FAB): MH$^+$ = 1243.

Application of this procedure to ethanol, n-butanol, allyl alcohol and hexyl alcohol results in the compounds ethyl-, butyl-, allyl- and hexylamycin.

5. Preparation of the $R^3$ alkyl-demalonyl derivatives ($R^1$, all $R^2$ and $R^4$=H; $R^3$=alkyl) and the diethyl compound ($R^1$ and all $R^2$=H; $R^3$ and $R^4$=alkyl)

500 mg of demalonyl compound from Example 3 are added to a mixture of 0.1 ml of acetyl chloride in 5 ml of ethanol, and the mixture is stirred at room temperature for 20 min. The ethanolic solution is chromatographed directly on silica gel using chloroform/methanol (8:2; v:v). 400 mg (80%) of $R^3$ ethyl-demalonyl derivative and 70 mg (14%) of the diethyl compound are obtained.

$R^3$ ethyl-demalonyl derivative: MS (FAB) MH$^+$ = 1085.

Diethyl compound: MS (FAB) MH$^+$ = 1113.

Application of an analogous procedure to propanol, n-butanol, allyl alcohol an n-hexyl alcohol yields the corresponding derivatives.

6. Preparation of the compound of the formula Ib 500 mg of sodium borohydride are added to 500 mg of demalonyl compound from Example 3 in 50 ml of methanol, and the mixture is stirred at room temperature for 24 hours. The excess sodium borohydride is decomposed by addition of glacial acetic acid. Removal of the solvent by distillation, and chromatography on dextran (®Sephadex LH 20) using methanol as eluent yields 450 mg (90%) of the compound of the formula Ib in which $R^1$ and all $R^2$ denote hydrogen.

MS (FAB) MH$^+$ = 1159.

Analogous reduction of amycin yields 420 mg (84%) of the compound of the formula Ib in which $R^1$ and one $R^2$ denote malonyl, and the remaining $R^2$ denote hydrogen.

MS (FAB) MH$^+$ = 1231.

7. Use of amycin and the corresponding demalonyl compound as fungicidal agent (a) Filter paper discs of diameter 6 mm are each uniformly wetted with 20 μl of active compound according to Examples 2 and 3 in various concentrations (see Tables 1 and 2), and placed on an agar medium which differs according to the species of fungus. Beforehand, while the agar is still in the liquid state, 0.5 ml of a suspension culture of the test organism (about $10^5$–$10^6$ conidia/1 ml) is added to each Petri dish (10 ml of agar, diameter 90 mm), and the 10 treated agar plates are then incubated at 25° C. After incubation for 3 to 4 days, the inhibition zone is measured as a measure of the inhibition of fungi and is reported in mm. A 10 mm inhibition zone is expressed as the MIC (minimum inhibitory concentration) of the relevant active compound in ppm of active compound.

The activity of the active compounds is expressed as a percentage, compared with the untreated infected control.

TABLE 3

| Concentration in ppm of active compound | Activity [%] of amycin according to Example 2 against Botrytis cinerea at ppm of active compound BCM- and Iprodion-sensitive (s) and resistant (r) strain | |
|---|---|---|
| | s | r |
| 1000 | 95 | 95 |
| 500 | 90 | 95 |
| 250 | 90 - (85) | 95 |
| 125 | 90 | 95 |
| 60 | 40 | 65 |
| control | 0 | 0 |

TABLE 4

Activity [%] of the demalonyl compund of Example 3 against Botrytis cinerea at ppm of active compound BCM- and Iprodion-sensitive (s) and resistant (r) strain

| Concentration in ppm of active compound | s | r |
|---|---|---|
| 1000 | 70 | 90 |
| 500 | 65 | 85 |
| 250 | 65 | 80 |
| 125 | 40 | 65 |
| 60 | 0 | 0 |
| control | 0 | 0 |

TABLE No. 1

Quantitive bioassay of amycin according to Example 2
Diameter of the bioactivity zone (mm)/20 μl on filter paper disc

| Concentration ppm (μl/ml) | Botrytis cinerea sensitive | Botrytis cinerea resistant | Cercospora beticola | Piricularia oryzae | Alternaria alternata | Fusarium culmorum | Penicillium digitatum |
|---|---|---|---|---|---|---|---|
| 2000 | 28 | 26 | 22 | 28 | 34 | 18 | 12 |
| 1000 | 24 | 24 | 20 | 26 | 28 | 16 | 10/12* |
| 500 | 22 | 18 | 10 | 20 | 26 | 14 | 12* |
| 250 | 16 | 12 | 12/16* | 18 | 22 | 14/16* | 10* |
| 125 | 12 | 12* | 16* | 14 | 16 | 12* | 0 |
| 60 | 10 | 10* | 14* | 10 | 14 | 10* | 0 |
| 30 | 10 h | 0 | 12* | 14* | 12* | 0 | 0 |
| 15 | 0 | 0 | 0 | 0 | 0 | 0 | 0 |

*incomplete inhibition but stuned mycelium

TABLE No. 2

Quantitative bioassay of the demalonyl compound according to Example 3
Diameter of the bioactivity zone (mm)/20 μl on filter paper disc

| Concentration ppm (μl/ml) | Botrytis cinerea sensitive | Botrytis cinerea resistant | Cercospora beticola | Piricularia oryzae | Alternaria alternata | Fusarium culmorum | Penicillium digitatum |
|---|---|---|---|---|---|---|---|
| 2000 | 14 | 16 | 14 | 16 | 16 | 12 | 10 |
| 1000 | 12 | 14 | 12 | 14 | 14 | 10 | 8 |
| 500 | 12 | 12 | 10 | 12 | 12 | 10 | 8/10* |
| 250 | 10/12* | 10/12* | 10 | 12 | 12 | 10 | 10* |
| 125 | 12* | 12* | 10* | 8 | 10* | 0 | 0 |
| 60 | 10* | 10* | 0* | 0 | 0 | 0* | 0 |
| 30 | 0 | 0 | 0 | 0 | 0 | 0 | 0 |

(b) Field beans (variety "Herz Freya" or "Frank's Ackerperle") are raised at about 26° to 28° C. and 60% relative humidity. The plants are suitable for the tests 14 days after sowing (height of growth 13 to 16 cm). After the plants have been prepared for the test, the test products according to Examples 2 and 3 are applied in the concentrations indicated in Tables 3 and 4, using a glass spray under an excess pressure of 0.3 to 0.5 bar, to the leaves of the field beans. The treated plants are put aside to dry and are inoculated about 3 hours later.

Suspensions of spores containing $4\times10^5$ spores per 1 ml are prepared with the fresh conidia of *Botrytis cinerea*. Then a glass spray producing a fine spray is used to apply the suspension of spores uniformly to the *Vicia faba* plants. The plants are placed in an air-conditioned cabinet at 20° to 22° C. and approximately 99% relative humidity. Infection of plants is manifested by the formation of black spots on leaves and stems, and severe infection causes the plants to collapse. The tests are evaluated 3 or 6 days after the inoculation.

(c) Apple understocks (EM IX) in the 4-leaf stage were uniformly treated with the compounds listed in the following table, in the application concentrations of 500, 250, 125, 60 and 30 mg of active compound/liter of spray mixture.

After the active compound coating had dried on, plants were heavily inoculated with conidia of apple scab (*Venturia inaequalis*) an placed, dripping wet, in an air-conditioned cabinet whose temperature was about 22° C. and whose relative humidity was about 100%. After an infection time of 48 hours, the plants were placed in a greenhouse at about 18° C. and a relative humidity of 95–100%.

After an incubation time of 14 days, the plants were examined for infestation wih apple scab (*Venturia inaequalis*). The infestation was assessed as usual by visual inspection. The activity of the active compounds on apple scab is expressed as a percentage, compared with the untreated infected control.

TABLE 7

| Active compound according to Examples 2 and 3 | Activity [%] on scab (Venturia inaequalis) with active compound [ppm] | | | | |
|---|---|---|---|---|---|
| | 500 | 250 | 125 | 60 | 30 |
| Amycin | 90 | 85 | 75 | 40 | 40 |
| Demalonyl derivative | 75 | 65 | 40 | 40 | 0 |
| Untreated infected plants | | | | | 0 |

8. Comparison of the fungicidal action of amycin and of the demalonyl compound with niphimycin The procedure is as in Example 7a, but niphimycin is used as test substance.

The results are listed in Table 8 which follows.

TABLE No. 8

| | Quantitative bioassay of niphimycin Diameter of the bioactivity zone (mm)/20 μl on filter paper disc | | | | | | |
|---|---|---|---|---|---|---|---|
| Concentration ppm (μl/ml) | *Botrytis cinerea* sensitive | *Botrytis cinerea* resistant | *Cercospora beticola* | *Piricularia oryzae* | *Alternaria alternata* | *Fusarium culmorum* | *Penicillium digitatum* |
| 2000 | 24 | 24 | 24 | 28 | 28 | 14 | 12 |
| 1000 | 20 | 18 | 18 | 22 | 20 | 10 | 10/12* |
| 500 | 14 | 10 | 12 | 18 | 14 | 12* | 12* |
| 250 | 10 | 12 | 10 | 12 | 12 | 10* | 10* |
| 125 | 10* | 0 | 0 | 10* | 10* | 0 | 0 |
| 60 | 0 | 0 | 0 | 0 | 0 | 0 | 0 |

*incomplete inhibition but stunted mycelium

We claim:

1. A compound selected from the group consisting of the formula Ia

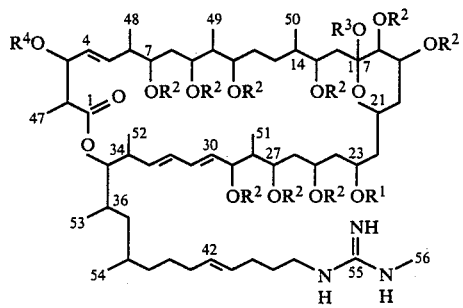

wherein
(a) $R^1$ and one $R^2$ are malonyl, while the remaining $R^2$ groups are hydrogen, $R^3$ is hydrogen and $R^4$ is hydrogen or $C_1$ to $C_6$ alkyl or allyl;
(b) $R^1$, $R^2$, $R^3$ are hydrogen and $R^4$ is hydrogen or $C_1$ to $C_6$ alkyl or allyl;
(c) $R^1$ and one $R^2$ are malonyl, $R^3$ is $C_1$ to $C_6$ alkyl, and $R^4$ is $C_1$ to $C_6$ alkyl or allyl; and
(d) $R^1$ is malonyl, $R^2$ is hydrogen and $R^3$ and $R^4$ are $C_1$ to $C_6$ alkyl and the compound of the formula IIa which is unsaturated in the 22/23 position

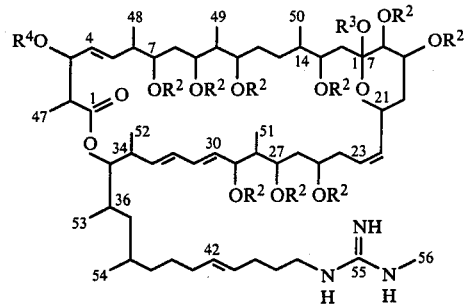

wherein
(e) $R^2$, $R^3$ and $R^4$ are defined as under (a)
(f) $R^2$, $R^3$ and $R^4$ are defined as under (b)
(g) $R^2$, $R^3$ and $R^4$ are defined as under (c) and
(h) $R^2$, $R^3$ and $R^4$ are defined as under (d)

and the compound of the formula Ib

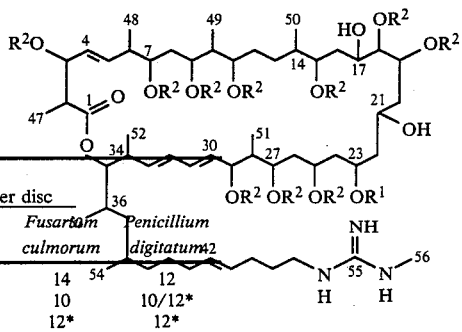

wherein
(i) $R^1$ and one $R^2$ are malonyl, while the remaining $R^2$ groups are hydrogen;
(j) $R^1$ is hydrogen and one $R^2$ is malonyl, while the remaining $R^2$ groups are hydrogen; and
(k) $R^1$ is malonyl and $R^2$ is hydrogen and the compound of formula IIb

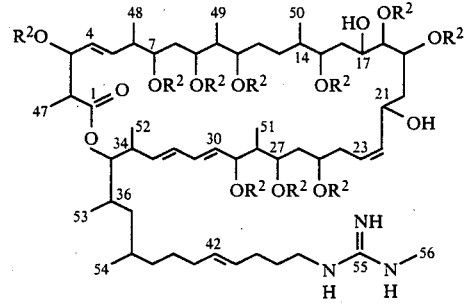

wherein
- (l) one $R^2$ is malonyl, while the remaining $R^2$ groups are hydrogen and
- (m) $R^2$ is hydrogen, and wherein the numbers 47 to 54 and 56 in each of formulas Ia, Ib, IIa and IIb represent a methyl group.

2. The compound of the formula Ia as claimed in claim 1 in which $R^1$ and one $R^2$ are malonyl and $R^3$ and $R^4$ are hydrogen.

3. The compound of the formula Ia as claimed in claim 1 in which $R^1$, $R^2$, $R^3$ and $R^4$ are hydrogen.

* * * * *